(12) United States Patent
Boersma et al.

(10) Patent No.: US 7,252,934 B2
(45) Date of Patent: Aug. 7, 2007

(54) SYNERGISTIC ACTIVATION OF REGULATORY ELEMENTS BY REL PROTEINS AND A STEROID RECEPTOR

(75) Inventors: Christine J. C. Boersma, Oosterbeek (NL); Paulus Theodorus Maria Van Der Saag, EA Maarn (NL); Sacha Wissink, Hertogenbosch (NL); Bart Van Der Burg, Houten (NL)

(73) Assignee: N.V. Organon, Oss (NL)

( * ) Notice: Subject to any disclaimer, the term of this patent is extended or adjusted under 35 U.S.C. 154(b) by 231 days.

(21) Appl. No.: 10/220,709

(22) PCT Filed: Mar. 6, 2001

(86) PCT No.: PCT/EP01/02585

§ 371 (c)(1),
(2), (4) Date: Nov. 18, 2002

(87) PCT Pub. No.: WO01/67110

PCT Pub. Date: Sep. 13, 2001

(65) Prior Publication Data

US 2003/0119717 A1 Jun. 26, 2003

(30) Foreign Application Priority Data

Mar. 8, 2000 (EP) .................... 00200815

(51) Int. Cl.
*C12Q 1/68* (2006.01)
*C12N 15/00* (2006.01)
*C12N 15/09* (2006.01)
*C12N 15/63* (2006.01)
*C12N 15/70* (2006.01)

(52) U.S. Cl. .................... 435/6; 435/320.1; 435/325
(58) Field of Classification Search .................... 435/6, 435/320.1, 325
See application file for complete search history.

(56) References Cited

U.S. PATENT DOCUMENTS 5,610,174 A * 3/1997 Craig et al. .................. 514/401
6,646,115 B1 * 11/2003 Montminy .................. 536/23.5

FOREIGN PATENT DOCUMENTS

EP 0 892 048 A 1/1999
WO 97 30083 A 8/1997

OTHER PUBLICATIONS

Goettlicher Martin et al: "Transcriptional cross-talk, the second mode of steroid hormone receptor action." Journal of Molecular Medicine (Berlin), vol. 76, No. 7, Jun. 1998, pp. 480-489.
Palvimo Jorma J et al: "Mutual transcriptional interference between RelA and androgen receptor." Journal of Biological Chemistry, vol. 271, No. 39, 1996, pp. 24151-24156.
Stein Bernd et al: "Repression of the Interleukin-6 Promoter by Estrogen Receptor is Mediated by NF-kappa-B and C/EBP-beta." Molecular and Cellular Biology, vol. 15, No. 9, 1995, pp. 4971-4979.
Sheppard Kelly-Ann et al: "Transcriptional activation by NF-kappaB requires multiple coactivators." Molecular and Cellular Biology, vol. 19, No. 9, 1999, pp. 6367-6378.
Na Soon-You et al: "Steroid receptor coactivator-1 interacts with the p50 subunit and coactivates nuclear factor kappaB-mediated transactivations." Journal of Biological Chemistry, vol. 273, No. 18, May 1, 1998, pp. 10831-10834.
Caldenhoven et al., "Negative Cross-Talk between RelA and the Glucocorticoid Receptor: A Possible Mechanism for the Antiinflammatory Action of Glucocorticoids," Molecular Endocrinology, vol. 9, No. 4, pp. 401-412 (1995).
Chamlers et al., "Comparative anatomical distribution of 5-HT$_{1A}$ receptor mRNA and 5-HT$_{1A}$ binding in rat-brain-a combined in situ hybridization/in vitro receptor autoradiographic study," Brain Research, 561 pp. 51-60 (1991).
Van Der Burg et al., "Mitogenic Stimulation of Human Breast Cancer Cells in a Growth Factor-Defined Medium: Synergestic Action of Insulin and Estrogen," Journal of Cellular Physiology, 134, pp. 101-108 (1988).
Kato et al., "Activation of the Estrogen Receptor Through Phosphorylation by Mitogen-Activated Protein Kinase," Science, vol. 270 pp. 1491-1494 (1995).
Greene et al., "Sequence and Expression of Human Estrogen Receptor Complementary DNA," Science, vol. 231, pp. 1150-1154 (1986).
Green et al., "Human oestrogen receptor cDNA: sequence, expression and homology to v-erb-A," Nature, vol. 320, pp. 134-139 (1986).
Webb et al., "Tamoxifen Activation of the Estrogen Receptor/AP-1 Pathway: Potential Origin for the Cell-Specific Estrogen-Like Effects of Antiestrogens," Molecular Endocrinology, vol. 9 No. 4, pp. 443-456 (1995).

(Continued)

*Primary Examiner*—James Ketter
(74) *Attorney, Agent, or Firm*—F. Aaron Dubberley (57) ABSTRACT

Interaction of Rel proteins and steroid receptors is known to result in repression of target genes. Here we describe the discovery of a new mechanism in which Rel proteins and steroid receptors act synergistically to activate a regulatory element. This mechanism is shown to influence the expression of the brain-specific 5HT1A receptor wherein the estrogen receptor acts synergistically with the Nuclear Factor kappa B to enhance the activity of the promoter for the 5HT1A receptor gene. In addition, synergistic effects of Rel proteins with the mineralocorticoid receptor were observed, showing that synergism with Rel proteins may be expected for other steroid receptors as well. The synergism between Rel proteins and estrogen receptor or mineralocorticoid receptor provides a tool for the development of compounds that interact with the estrogen or mineralocorticoid receptor in such a way that only the synergistic effect is modulated whereas other effects are left intact. Such compounds would be invaluable for the development of medicaments for the treatment of diseases of the central nervous or cardiovascular system and other disorders in which Rel proteins play a role.

10 Claims, 7 Drawing Sheets

OTHER PUBLICATIONS

Elgort et al., "Estrogen and Estrogen Receptor Antagonists Stimulate Transcription from the Human Retinoic Acid Receptor-α1 Promoter via a Novel Sequence," Molecular Endocrinology, vol. 10, No. 5, pp. 477-487 (1996).

Tzukerman et al., "Human Estrogen Receptor Transactivational Capacity is Determined by both cellular and Promoter Context and Mediated by Two Functionally Distinct Intramolecular Regions," Molecular Endocrinology, vol. 8, No. 1, pp. 21-30 (1994).

Pfahl et al., "Nuclear Retinoic Acid Receptors: Cloning, Analysis, and Function," Methods in Enzymology, vol. 189, pp. 256-270 (1990).

Wissink et al., "NF-kB/Rel Family Members Regulating the ICAM-1 Promoter in Monocytic THP-1 Cells," Immunobiol, vol. 198 (pp. 50-64 (1997).

Fink et al., "Sex Steroid Control of Mood, Mental State and Memory," Clinical and Experimental Pharmacology and Physiology, 25, pp. 764-775 (1998).

Gregoire et al., "Transdermal oestrogen for treatment of severe postnatal depression," The Lancet, vol. 347, pp. 930-933 (1996).

Chen et al., "A novel DNA recognition mode by the NF-kB p65 homodimer," Nature Structural Biology, vol. 5, No. 1, pp. 67-73 (1998).

Oppenheim, "Estrogen in the Treatment of Depression: Neuropharmacological Mechanisms," Biological Psychiatry, vol. 18, No. 6, pp. 721-725 (1983).

Gitlin et al., "Psychiatric Syndromes Linked to Reproductive Function in Women: A Review of Current Knowledge," Am J Psychiatry, vol. 146 No. 11, pp. 1413-1422 (1989).

Bethea et al., "Ovarian Steroids and Serotonin Neural Function," Molecular Neurobiology, vol. 18, pp. 87-123 (1998).

Maes et al., "The Serotonin Hypothesis of Major Depression," Psychopharmacology, The 4$^{th}$ Generation of Progress, Chapter 81, pp. 933-944 (1995).

Murphy, "Neuropsychiatric Disorders and the Multiple Human Brain Serotonin Receptor Subtypes and Subsystems," Neuropsychopharmacology, vol. 3, No. 5/6, pp. 457-471 (1990).

Albert t al., "Cloning, Functional Expression, and mRNA Tissue Distribution of the Rat 5-Hydroxytryptamine$_{1A}$ Receptor Gene," The Journal of Biological Chemistry, vol. 265, No. 10, pp. 5825-5832 (1990).

Biegon et al., "Modulation By Estradiol Of Serotonin$_1$ Receptors In Brain," The Journal of Neuroscience, vol. 2, No. 2, pp. 199-205 (1982).

Buhot, "Serotonin receptors in cognitive behaviors," Current Opinion in Neurobiology, vol. 7, pp. 243-254 (1997).

Danielian et al., "Identification of a conserved region required for hormone dependent transcriptional activation by steroid hormone receptors," The EMBO Journal, vol. 11, No. 3, pp. 1025-1033 (1992).

Fargin et al., Effector Coupling Mechanisms of the Cloned 5-HT1A Receptor, The Journal of Biological Chemistry, vol. 264, No. 25, pp. 14848-14852 (1989).

Galien et al., "Involvement of CCAAT/Enhancer-Binding Protein and Nuclear Factor-kB binding Sites in Interleukin-6 Promoter Inhibition by Estrogens," Molecular Endocrinology, vol. 10, No. 6 (1996).

Harrison et al., "Synergistic Activation of Neurotensin/Neuromedin N Gene Expression by c-Jun and Glucocorticoids: Novel Effects of Fos Family Proteins," Molecular Endocrinology, vol. 9, No. 8, pp. 981-993 (1995).

Hu et al., "Inhibition of Adipogenesis Through MAP Kinase-Mediated Phosphorylation of PPARγ," Science, vol. 274, pp. 2100-2103 (1996).

Joffe et al., "A Decade Of Serotonin Research: Regulation Of Affect and Eating Behavior. Estrogen, Serotonin, and Mood Disturbance: Where is the Therapeutic Bridge?," Society of Biological Psychiatry, vol. 44, pp. 798-811 (1998).

Jonat et al., "Antitumor Promotion and Antiinflammation: Down-Modulation of AP-1 (Fos/Jun) Activity by Clucocorticoid Hormone," Cell, vol. 62, pp. 1189-1204 (1990).

Julis,"Molecular Biology Of Serotonin Receptors," Annual Review of Neuroscience, vol. 14, pp. 335-360 (1991).

Krishnan et al., "Estrogen Receptor-Sp1 Complexes Mediate Estrogen-induced Cathepsin D Gene Expression in MCF-7 Human Breast Cancer Cells," The Journal of Biological Chemistry, vol. 269, No. 22, pp. 15912-15917 (1994).

Kuiper et al., "Cloning of a novel estrogen receptor expressed in rat prostate and ovary," Proc. Natl, Acad. Sci. USA, vol. 93, pp. 5925-5930 (1996).

Kunsch et al., "Selection of Optimal kB/Rel DNA-Binding Motifs: Interaction of Both Subunits of NF-kB with DNA Is Required for Transcriptional Activation," Molecular and Cellular Biology, vol. 12, No. 10, pp. 4412-4421 (1992).

Le Goff et al., "Phosphorylation of the Human Estrogen Receptor," The Journal of Biological Chemistry, vol. 269, No. 6, pp. 4458-4466 (1994).

Legler et al., Development of a Stably Transfected Estrogen Receptor-Mediated Luciferase Receptor Gene Assay in the Human T47D Breast Cancer Cell Line, Toxicological Sciences, vol. 48, pp. 55-66 (1999).

Mcewen et al., "Estrogen Actions in the Central Nervous System," Endocrine Reviews, vol. 20, No. 3, pp. 279-607 (1999).

McInerney et al., "Transcription Activation by the Human Estrogen Receptor Subtype β(ERβ) Studied with ERβ and ERα Receptor Chimeras," Endocrinology, vol. 139, No. 11, pp. 4513-4522 (1998).

McQueen et al., "Estradiol-17β increases serotonin transporter (SERT) mRNA levels and the density of SERT-binding sites in female rat brain," Molecular Brain Research, vol. 45, pp. 13-23 (1997).

Mosselman et al., "ERβ: identification and characterization of a novel human estrogen receptor," FEBS Letters, vol. 392 pp. 49-53 (1996).

O'Neill et al., "NF-kB: a crucial transcription factor for glial and neuronal cell function," Trends Neuroscience, vol. 20, pp. 252-258 (1997).

Reichert et al., "Building a brain: development insights in insects," Trends Neuroscience, vol. 20, pp. 258-264 (1997).

Parry et al, "A Set of Inducible Genes Expressed by Activated Human Monocytic and Endothelial Cells Contain kB-like Sites That Specifically Bind c-Rel-p65 Heterodimers," The Journal of Biological Chemistry, vol. 269, No. 33, pp. 20823-20825 (1994).

Pompeiano et al., "Distribution and Cellular Localization of mRNA Coding for 5-HT$_{1A}$ Receptor in the Rat Brain: Correlation with Receptor Binding," The Journal of Neuroscience, vol. 12, No. 2, pp. 440-453 (1992).

Ray et al., "Down-modulation of Interleukin-6 Gene Expression by 17β-Estradiol in the Absence of High Affinity DNA Binding by the Estrogen Receptor," The Journal of Biological Chemistry, vol. 269, No. 17, pp. 12940-12946 (1994).

Schmidt-Ulrich et al., "NF-kB activity in transgenic mice: developmental regulation and tissue specificity," Development, vol. 122, pp. 2117-2128 (1996).

Shughrue et al., "Comparative Distribution of Estrogen Receptor-α -β mRNA in the Rat Central Nervous System," The Journal of Comparative Neurology, vol. 388, pp. 507-525 (1997).

Stein et al., "Repression of the Interleukin-6 Promoter by Estrogen Receptor Is Mediated by NF-kB and C/EBPβ," Molecular And Cellular Biology, vol. 15, No. 9, pp. 4971-4979, Sep. (1995).

Tora et al., "The Human Estrogen Receptor Has Two Independent Nonacidic Transcriptional Activation Functions," Cell, vol. 59, pp. 477-487 (Nov. 3, 1989).

Tremblay et al., "Ligand-Independent Recruitment of SRC-1 to Estrogen Receptor β through Phosphorylation of Activation Function AF-1," Molecular Cell, vol. 3, pp. 513-519 (Apr. 1999).

Wissink et al., "Distinct Domains of the ReIA NF-kB Subunit Are Required for Negative Cross-talk and Direct Interaction with the Glucocorticoid Receptor," The Journal of Biological Chemistry, vol. 272, No. 35 pp. 22278-22284 (Aug. 29, 1997).

Albert et al., "Cloning, Functional Expression, and mRNA Tissue Distribution of the Rat 5-Hydroxytryptamine$_{1A}$ Receptor Gene," The Journal of Biological Chemistry, vol. 265, No. 10, pp. 5825-5832 (Apr. 5, 1990).

Collins et al., "Structure and Chromosomal Location of the Gene for Endothelial-Leukocyte Adhesion Molecule 1," The Journal of Biological Chemistry, vol. 266, No. 4, pp. 2466-2473 (Feb. 5, 1991).

Kaszubska et al., "Cyclic AMP-Independent ATF Family Members Interact with NF-kB and Function in the Activation of the E-Selectin Promoter in Response to Cytokines," Molecular and Cellular Biology, vol. 13, No. 11, pp. 7180-7190 (Nov. 1993).

Paech et al., "Differential Ligand Activation of Estrogen Receptors ERα and ERβ at AP1 Sites," Science, vol. 277, pp. 1508-1510 (Sep. 5, 1997).

* cited by examiner

SEQUENCE LISTING

<160> NUMBER OF SEQ ID NOS: 4

<210> SEQ ID NO 1
<211> LENGTH: 21
<212> TYPE: DNA
<213> ORGANISM: Artificial sequence
<220> FEATURE:
<223> OTHER INFORMATION: primer

<400> SEQUENCE: 1
gagccgaatt ctacagacta a                                          21

<210> SEQ ID NO 2
<211> LENGTH: 29
<212> TYPE: DNA
<213> ORGANISM: Artificial sequence
<220> FEATURE:
<223> OTHER INFORMATION: primer

<400> SEQUENCE: 2
aactgcaagg agatctacat cgcccctcg                                  29

<210> SEQ ID NO 3
<211> LENGTH: 67
<212> TYPE: DNA
<213> ORGANISM: Artificial sequence
<220> FEATURE:
<223> OTHER INFORMATION: primer

<400> SEQUENCE: 3
catacggtaa gcttggggtc atcgccctgc caccgccgcc cgattgcttt agcttggaaa    60
ttccgga                                                              67

<210> SEQ ID NO 4
<211> LENGTH: 67
<212> TYPE: DNA
<213> ORGANISM: Artificial sequence
<220> FEATURE:
<223> OTHER INFORMATION: primer

<400> SEQUENCE: 4
gtatgccaaa gcttctccgg aatttccaag ctccggaatt tccaagctcc ggaatttcca    60
agctaaa                                                              67

SYNERGISTIC ACTIVATION OF REGULATORY ELEMENTS BY REL PROTEINS AND A STEROID RECEPTOR

FIELD OF THE INVENTION

The invention relates to a method for the identification of compounds capable of modulating a newly discovered-mechanism whereby a steroid receptor and a Rel protein act synergistically to activate a regulatory element. The invention also relates to a cell transfected with nucleic acid and the use of that cell in an assay for the identification of compounds that modulate the level of gene expression under the control of the regulatory element as well as the medical use of compounds identified in such an assay.

BACKGROUND OF THE INVENTION

Members of the Nuclear Factor-κB (NF-κB)/Rel family of transcription activator proteins are tightly associated with their inhibitory proteins (I-κB) and reside in the cytoplasm. They can be induced by pro-inflammatory cytokines and are important in immunological and inflammatory processes because they direct transcription of chemoattracants, cytokines (including the NF-κB induced cytokines themselves), cytokine receptors and cell adhesion molecules. Upon induction, rel proteins dimerize and migrate to the nucleus where they activate their target genes through an NF-κB binding motif in the promoter of these genes. Examination of DNA sequences recognized by different NF-κB dimers reveals that the prefered target sites are slightly different for the existing dimer combinations of rel proteins (Chen et al., —Nature Struct. Biol. 5: 67–73, 1998; Kunsch et al., Mol. Cell Biol. 12: 4412–4421, 1992; Parry and Mackman, J. Biol. Chem. 269: 20823–20825, '94), explaining the broad variation in NFκB responsive elements that have been identified in various promoters.

Dimerization and nuclear translocation of Rel proteins is induced by a large number of agents including bacterial and viral pathogens, immune and inflammatory cytokines and a variety of agents that damage cells. An even larger number of genes appear to be targets for the activation by Rel proteins, as this family of transcription factors has been found to interact with steroid receptors such as estrogen receptors and glucocorticoid receptors, resulting in repression of target genes.

Estrogen and other steroids have profound effects on the central nervous system (1). Particularly, the ability of estrogen to modulate the brain serotonin system suggests that estrogens may play a role in the mechanism associated with depression and its treatment (2, 3). However, as ER expression is widely distributed, it is not surprising that estrogens have several other benificial effects, including the protection against atherosclerosis, Alzheimer dementia and osteoporosis. In order to limit the risk on side effects, such as an enhanced risk on breast and endometrium cancer due to treatment with estrogens, a considerable amount of effort is invested in the search for tissue-selective ER-binding compounds.

Apart from estrogens, much interest exists in tissue-selective effects of other steroid receptors. Also for these steroid receptors the development of compounds that exclusively target one set of tissues or organs (e.g. brain for psychiatric illnesses) has been hampered by the wide tissue distribution of most types of steroid receptors. For this reason much interest exists in assays that would allow for screening of steroid receptor-mediated effects in a tissue selective fashion.

The effects of estrogen are known to be mediated by two estrogen receptors (ERα and β), that belong to the superfamily of nuclear hormone receptors (15–18). The two ERs share a well-conserved modular structure. While the DNA-binding domain is highly conserved between ERα and β (96% identity) and the ligand-binding domain is relatively well conserved (58% identity), the A/B region is poorly conserved between the two receptors (20% identity). Upon ligand binding, the activated receptor dimerizes and interacts with specific DNA sequences, termed estrogen response elements (EREs), located in the regulatory region of target genes. The DNA-bound receptor can then regulate transcription either positively or negatively. It is known for ERα that the regulation of transcription is mediated by two transactivation regions: AF-1 located in the A/B domain and AF-2 located in the ligand-binding domain. The two transactivation regions may function independently or cooperate, depending on cell and promoter context (19, 20). Recently some other mechanisms have been discovered by which estrogen regulates target genes. These include genes that utilize regulatory elements as the target sequence of ER action (21) or genes that are regulated by ER through interaction with other transcription factors bound to their respective DNA-binding sites, such as AP-1 and Sp 1 (22–23, 36–38).

SUMMARY OF THE INVENTION

We report here the discovery of a mechanism in which NF-κB and members of the steroid receptor family act synergistically to activate gene expression by interaction with a variety of regulatory elements. Such synergistic activation has so far not been described, many reports however, deal with the mutual inhibition of Rel proteins and steroid receptors. The newly discovered mechanism provides the necessary tools to develop compounds that modulate the expression of regulatory elements. Depending on the regulatory element, such compounds may act through omnipresent steroid receptors and yet provide for a tissue selective response.

DETAILED DESCRIPTION OF THE INVENTION

As a first example, we investigated the molecular mechanism by which estrogen modulates the serotonin system. More in particular, we have investigated the effect of estrogen on the 5-HT1A receptor gene. Serotonin (5-hydroxytryptamine, 5-HT) is involved in the control of a variety of behavioral processes (4). Dysregulation, of the serotonin system is thought to play an important role in neuropsychiatric disorders, such as depression and anxiety (5, 6). The complex action of serotonin is mediated by a large family of related receptors (7). Particular attention has focused on the 5HT1A receptor, which is a G protein coupled receptor that negatively regulates adenylate cyclase (8). The 5-HT1A receptor is expressed in a restricted pattern in the brain and high levels of receptors were observed in the limbic areas, cerebral cortex and raphe nuclei of the brain (9–11). Here we show that ERα acts synergistically with NF-κB to activate the 5-HT1A receptor promoter. This activation already occurred in the absence of hormone and could be further induced by the addition of either 17β-estradiol ($E_2$) or 4-hydroxytamoxifen (OH-T), but not by ICI 164384. ERβ was also able to mediate this effect although the effect of ERα in this example was far more profound. Furthermore, we found that this synergistic activation was dependent both on the transactivation domains of the p65 subunit of NF-κB and the A/B domain of ERα, containing AF-1. Our findings show that estrogens may regulate the expression of the 5-HT1A receptor via a new mechanism involving synergistic activation by NF-κB with ER.

Figure 7:
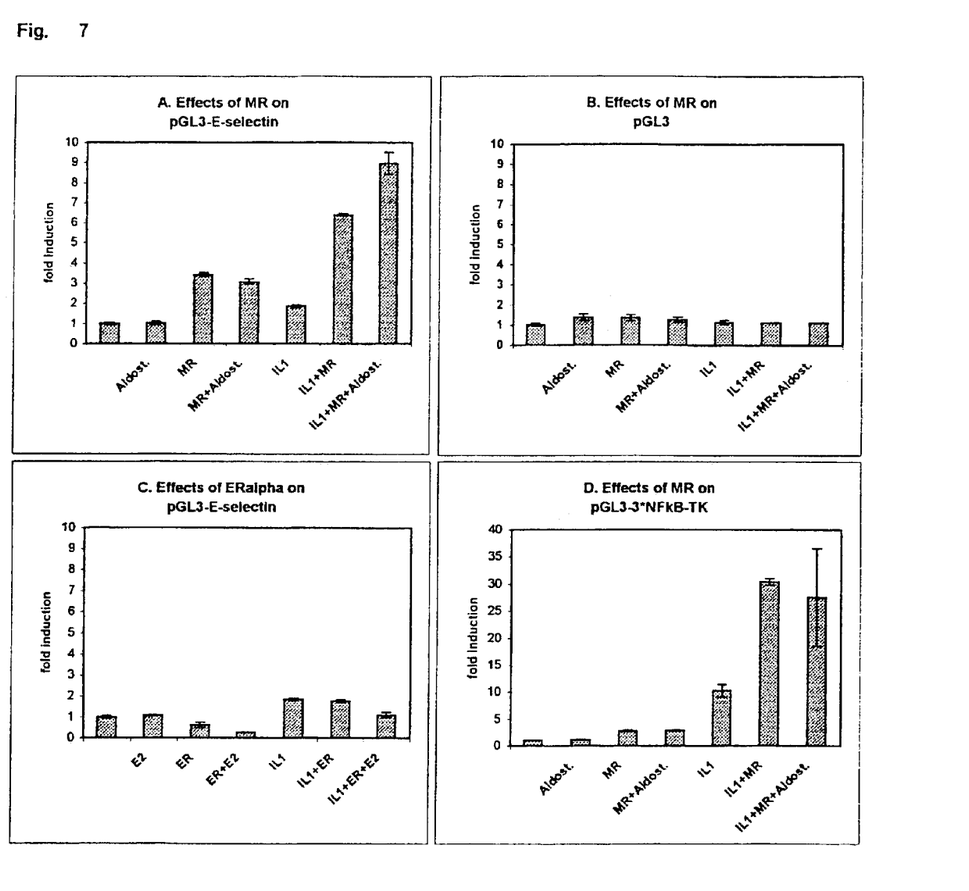

The same synergistic effect was surprisingly found to play a role in the activation of the E-selectin promoter by NF-κB and steroid receptors like the mineralocorticoid receptor (MR). This is detailed in FIG. 7 and in the text below. As it now appears that synergistic effects with NF-κB via regulatory elements is not restricted to ER, but is also observed with MR, similar results are to be expected with other steroid receptors.

The present invention opens the possibility to design screening assays for the identification of compounds capable of modulating the newly discovered mechanism. For instance, since the 5HT1A receptor is exclusively present in brain tissue and E-Selectin is only expressed by endothelial cells, ligands found in such assays may specifically be used to treat CNS diseases and/or cardiovascular diseases and thus permit the identification of compounds that act in a tissue-selective manner. Assays for the deselection of such ligands which target other tissues are available and known to the skilled person.

In the present study, we also show that the cis-regulatory region of the 5-HT1A receptor contains two putative NF-κB binding sites and the presence of NF-κB proteins is critical for synergistic induction by ER. This shows that NF-κB complexes cooperate with ER to synergistically regulate 5-HT1A receptor gene expression. In most systems that have been examined so far, the estrogen and NF-κB signaling pathways are mutually antagonistic. For instance, regulation of the IL-6 promoter has been extensively studied and NF-κB-induced activation of this gene could clearly be inhibited by estrogen (33, 34). Consistent with these findings, we have shown that on an artificial NF-κB reporter construct and on the E-selectin promoter (FIG. 7) estrogen inhibits NF-κB activity. However, on the 5-HT1A receptor promoter estrogen further enhanced NF-κB-induced activity, indicating that positive or negative regulation by estrogen is dependent on the promoter context.

ERα and ERβ show a high degree of homology in the DNA-binding domain and moderate homology in the ligand-binding domain, however, the A/B region is poorly conserved between the two receptors. Based on several different approaches, synergistic activation of the 5-HT1A receptor promoter by NF-κB and ER was found to be dependent on the N-terminal region of ERα, containing AF-1. First, replacement of the A/B region of ERβ with the A/B region of ERα (ERα/β) resulted in a chimeric receptor which was even more potent than wildtype ERα in activation of the 5-HT1A receptor promoter. However, replacement of the A/B region of ERα with the A/B region of ERβ (ERβ/α) almost completely abolished the ability of the receptor to synergistically activate the promoter. Second, synergistic activation by ERα 1–339, an AF-2 defective mutant, was comparable to wildtype ERα, while effects of ERα 121–599, an AF-1 defective mutant, were comparable to wildtype ERβ. Third, effects of ERβ in mediating this synergistic effects were, in comparison to ERα, much smaller. Fourth, the partial anti-estrogen OH-T, which blocks only AF-2, was as potent as $E_2$ in activation of the 5-HT1A receptor promoter. The AF-1-mediated agonistic effect of anti-estrogens has recently been reported to be mediated via the A/B region of ERα but not by the A/B region of ERβ (28). These differences between ERα and ERβ suggest different regulatory functions for the two ER subtypes. Taken together, these data show a clear involvement of ERα AF-1 in 5-HT1A receptor promoter regulation.

Our findings clearly show a crucial role for NF-κB complexes and NF-κB binding sites in the synergistic activation of the 5-HT1A receptor promoter by ER. However, mutation of the two NF-κB elements in the −901luc construct abolished the NF-κB effect while the ER effect was maintained. One explanation could be that NF-κB proteins bind as monomers to these mutated κB elements. This NF-κB-DNA complex, unable to activate transcription in this conformation, might be stabilized by ER and consequently results in activation, possibly in concert with other responsive sequences in the promoter of the 5-HT1A receptor gene. Furthermore, it is evident from the use of ERα mutants and chimeras that, although a functional DNA binding domain of ERα is required, there is no clear correlation between ERα activity on the ERE reporter and the 5-HT1A receptor promoter. Therefore, the most likely explanation for the synergistic activation of the 5-HT1A receptor promoter is that ER activates this promoter not via direct binding to DNA but via protein-protein interactions. This model is supported by the fact that both the DNA-binding domain of ERα and an intact RHD of p65 are required for the synergistic activation, since ERα has been described to directly interact with p65 involving the DNA-binding domain of ERα and the RHD Of p65 (34Furthermore, both the transactivation domains of p65 and AF-1 of ERα are essential for this response. Therefore, the present results suggest that NF-κB complexes cooperate with ER to recruit coactivators into the complex via AF-1 and thereby synergistically activate the 5-HT1A receptor promoter.

In addition to the classical hormone activation pathway other signal transduction pathways have been described to regulate a number of steroid receptors, including ERα, independently of hormonal ligands. Nuclear receptors have been shown to be activated by nonsteroidal agents, like dopamine, growth factors and PKA activators via phosphorylation (39). Phosphorylation of ERα was shown to enhance receptor activity and major phosphorylation sites are located in the A/B region of the receptor (40, 41). Recently it was demonstrated that phosphorylation of ERβ AF-1 regulates cofactor recruitment and gene activation by nonsteroidal activators (42), whereas phosphorylation of the A/B domain of peroxisome proliferator-activated receptor γ decreased its transcriptional activity (43). The presence of several kinase sites within the A/B region of ERα and ERβ suggests that differential phosphorylation of the AF-1 domain may result in diverse responses of the receptors by different activators. The existence of this additional pathway emphasizes the importance of AF-1 in hormone-independent receptor activation.

Several lines of evidence suggest that estrogen might also regulate 5-HT1A receptor expression in the CNS. For instance, the decline in estrogen prior to parturition and at the onset of menopause has been correlated with negative effect (44), while estrogen replacement therapy can in some cases alleviate depression or anxiety in women (45, 46). Moreover, ovariectomy caused decreases in 5-HT binding and 5-HT transporter binding sites (12–14), while replacement of estrogen to ovariectomized rats reversed this decline. Both ERα and ERβ have been identified in multiple regions of the brain, including the cortex, hippocampus and raphe nuclei (47). In addition, NF-κB has also been described to be active in the brain, particularly in the cortex and hippocampus (48). At the same time evidence is emerging that NF-κB not only functions in immune cells, but also has unique roles in processes such as neuronal plasticity, neurpdegeneration and neuronal development (49). Thus, these transcription factors and pathways may play an important role in regulation of 5HT1A receptor gene expression in the brain. The ability of estrogen to modulate serotonergic receptor function may underlie, at least in part, the profound effects of this hormone on mood and mental state.

Synergistic activation between steroid receptors and Rel proteins was also found with the E-selectin promoter. To determine the effects of mineralocorticoids on E-selectin promoter activity, we transiently transfected U-2 OS cells with a luciferase reporter construct containing part of the E-selectin promoter together with an expression vector encoding MR. As shown in FIG. 7A, IL-1β induced promoter activity was stimulated by MR in a synergistic fashion. This NF-κB induced activity of the E-selectin promoter in the presence of MR could be further enhanced by addition of aldosteron. Selectivity of this mechanism was shown by repeating the experiment with a luciferase vector without the E-selectin promoter. No effects of IL-1β and/or MR were observed (FIG. 7B).

Interestingly, if ERα was co-transfected instead of MR no synergistic effects on E-selectin promoter activity were observed. Instead, under these conditions the IL-1β induced promoter activity was repressed by ERα in the absence of ligand, which effect was further increased by addition of 17β-estradiol (FIG. 7C). These results show again that synergistic effects of ligand-activated steroid receptors with NF-κB's depend on the specific promoter context and selectivity for a particular steroid receptor-promoter combination.

The E-selectin promoter contains multiple NF-κB consensus sites (Collins, T., Williams, A., Johnston, G. I., Kim, J., Eddy, R., Shows, T., Gimbrone, M. A., Bevilacqua, M. P. (1991) J. Biol. Chem. 266: 2466–2473) that most probably are responsible for the synergistic effects of mineralocorticoids on the E-selectin promoter. The role of NF-κB in the above described synergistic effects with MR was confirmed by studies in which effects of mineralocorticoids are tested on a 3*NF-κB-TK reporter, a synthetic reporter construct that contains 3 copies of a consensus NF-κB binding site in front of the TK promoter (FIG. 7D). As indicated by the used scale of FIG. 7D, the synthetic 3*NF-κB-TK reporter is much more sensitive to both stimulation by IL-1β and the synergistic effect of MR. This is not surprising as this reporter contains multiple repeats of NF-κB responsive elements. Synergistic effects of rel proteins and MR are not further enhanced by addition of aldosteron, which may be due to the large synergistic effect of IL-1β and MR in the absence of aldosteron. The finding that MR and ER are able to induce or repress promoter activity in the absence of IL-1β (see FIGS. 7A, C and D the third and fourth bar) suggests that U-2 OS cells contain constitutively NF-κB activity in the absence of cytokines. Alternatively, U-2 OS cells may themselves produce cytokines or cytokine activity may be derived from the serum in which the cells are grown. Although it can not be excluded that also other types of transcription factors are involved in modulation of the E-selectin promoter and 3*NF-κB-tk reporter (Kaszubska, W., Hooft van Huijsduijnen, R., Ghersa, P., DeRaemy-Schenk, A.-M., Chen, B. P., Hai, T., Delamarter, J. F., Whelan, J. Mol. Cell. Biol. 13: 7180–7190), the above results at least show that NF-κB's play a crucial role in stimulation of these promoter-reporters by mineralocorticoids. The above described differences between ERα and MR, in either their synergy or antagonism with IL-1β induced Rel proteins, are likely to be due to differential activities of complexes that include either ERα or MR and different types of NF-κB's. In addition, the present study shows that different types of nuclear receptors can have synergistic effects with NF-κB's on NF-κB responsive promoters. The exact nature of the effect is clearly dependent on the combination of steroid receptor type and the nature of the promoter.

Now having described several specific embodiments of the invention, it is clear that a skilled person is enabled to select other regulatory elements that are synergistically activated by Rel proteins and steroid receptors. In brief this may best be done by cotransfection of the particular regulatory element under investigation functionally coupled to a reporter gene, together with expression vectors encoding a Rel protein and a steroid receptor. In particular expression vectors encoding NF-κB and a steroid receptor may be suited for that purpose. The steroid receptor may be ERα or MR, but also ERβ or a combination of ERα and ERβ. The examples provide the necessary tools to further select regulatory elements capable of being synergistically activated according to the invention.

The discovery of a new mechanism in which Rel proteins and steroid receptors interact in order to synergistically activate a regulatory element opens the possibility to screen for compounds that specifically interact with this new mechanism. The invention in one aspect therefore relates to a method for the identification of compounds capable of modulating a synergistic effect of a steroid receptor and a Rel protein on regulatory elements, comprising the steps of:
providing a cell comprising a regulatory element capable of being synergistically activated by a steroid receptor and a Rel protein, said cell additionally comprising sufficient levels of said steroid receptor and said Rel protein or functional equivalents thereof to allow synergistic activation of the regulatory element.

contacting said cell with at least one compound determining whether the activation of the regulatory element is modulated by the compound Compounds capable of modulating the synergistic effect of a Rel protein and an steroid receptor may be compounds that stimulate or inhibit the synergistic effect. Examples of known compounds capable of stimulating the synergistic effect of some steroid receptors and Rel proteins on the promotor of the serotonin 1A receptor or the E-selectin promoter are provided in the examples section.

Functional equivalents of Rel proteins in this respect are to be understood as a protein complex of the Rel family that share a homology in the Rel domain and are involved in gene regulation (Liou and Baltimore, Current Opinion in Cell Biology, 5: 477–487, 1993) including but not limited to NF-κB1, Lyt-10, cRel RelA and RelB. Also included are functional equivalents of NF-κB that retain a certain biological function, preferably fragments that contain at least the transactivation domain together with the DNA binding domain of NF-κB.

By "regulatory element" or "promoter" is meant a DNA sequence that is capable of binding directly or indirectly to RNA polymerase in a cell and initiating transcription of a downstream (3' direction) coding sequence.

A promoter may be linked to a heterologous reporter gene capable of signaling the activation of the regulatory element. In such a construct, the promoter influences the transcription from the heterologous gene Suitable reporter genes are for instance luciferase, chloramphenicol acetyl transferase, beta galactosidase and secreted placental alkaline phosphatase.

Functional equivalents of ER in this respect are to be understood as fragments of ER that at least contain the AF-1 transactivation region of ERα together with the DNA binding domain of ERα.

The term "functional equivalents" in general is to be understood as a molecule capable of excerting the same biological function as the molecule it refers to.

Levels of the steroid receptor and the Rel protein in the cell must be sufficient to exert synergistic activation of the regulatory, element. This may be achieved by choosing a suitable cell that constitutively synthesises steroid receptor and Rel protein in sufficient levels or in which steroid receptor and Rel protein expression can be induced by the addition of the appropriate factors. Alternatively, the steroid receptor and the Rel protein may be transfected into the cell using appropriate recombinant DNA vectors and transfection methods known in the art.

In a preferred embodiment, the invention relates to a method as described above, wherein said steroid receptor is selected from the group consisting of the estrogen receptor α, the estrogen receptor β and/or the mineralocorticoid receptor or functional equivalents thereof.

In a further preferred embodiment, the invention relates to a method as described above, wherein the Rel protein is selected from the group consisting of NF-κB, Lyt-10, cRel, RelA and RelB or functional equivalents thereof.

In a further preferred embodiment, the invention relates to a method as described above, wherein the regulatory element is a promoter for the 5HT1-A receptor gene or a functional equivalent thereof.

In a further preferred embodiment, the invention relates to a method as described above, wherein the regulatory element is a promoter for the E-selectin gene or a functional equivalent thereof.

In a further preferred embodiment, the invention relates to a method as described above, wherein said cell is transfected with a reporter gene capable of signaling the activation of the regulatory element.

The invention also relates to a cell transfected with nucleic acid comprising a promotor for the 5HT1A receptor gene or a functional equivalent thereof, said cell further comprising:
nucleic acid encoding a steroid receptor capable of functionally expressing said steroid receptor receptor or a functional equivalent thereof within said cell, and also comprising nucleic acid encoding a Rel protein or a functional equivalent thereof capable of functionally expressing said Rel protein within said cell.

The invention further relates to a cell according to the invention wherein said steroid receptor is selected from the group consisting of the estrogen receptor α, the estrogen receptor β and/or the mineralocorticoid receptor or functional equivalents thereof.

The invention further relates to a cell according to the invention wherein the Rel protein is selected from the group consisting of NF-κB, Lyt-10, cRel, RelA and RelB or functional equivalents thereof.

The invention further relates to a cell according to the invention wherein said cell is transfected with a reporter gene capable of signaling the activation of the promotor for the 5HT1A receptor gene.

The invention further relates to a cell according to the invention wherein the nucleic acid comprising a promotor for the 5HT1A receptor gene and/or the nucleic acid encoding a steroid receptor and/or the nucleic acid encoding a Rel protein or functional equivalents thereof are transfected into the cell The invention further relates to a cell transfected with nucleic acid comprising a promotor for the E-selectin gene or a functional equivalent thereof, said cell further comprising:
nucleic acid encoding a steroid receptor capable of functionally expressing said steroid receptor receptor or a functional equivalent thereof within said cell, and also comprising nucleic acid encoding a Rel protein or a functional equivalent thereof capable of functionally expressing said Rel protein within said sell.

The invention further relates to a cell according to the invention wherein said steroid receptor is selected from the group consisting of the estrogen receptor α, the estrogen receptor β and/or the mineralocorticoid receptor or functional equivalents thereof.

The invention further relates to a cell according to the invention wherein the Rel protein is selected from the group consisting of NF-κB, Lyt-10, cRel, RelA and RelB or functional equivalents thereof.

The invention further relates to a cell according to the invention wherein said cell is transfected with a reporter gene capable of signaling the activation of the promotor for the E-selectin gene.

The invention further relates to a cell according to the invention wherein the nucleic acid comprising a promotor for the E-selectin gene and/or the nucleic acid encoding a steroid receptor and/or the nucleic acid encoding a Rel protein or functional equivalents thereof are transfected into the cell, The invention further relates to the use of a cell as described above for the identification of compounds that modulate the level of serotonin receptor in the brain.

The invention also relates to compounds identified with the method described above for use as a medicament.

The invention also relates to the use of compounds identified with the method above for the preparation of a medicament for the treatment of diseases of the central nervous system.

In a preferred embodiment, compounds that modulate the synergistic effect of steroid receptors and Rel proteins do not affect the mechanisms in which Rel proteins or steroid receptors individually influence a regulatory element. These compounds provide a selectivity which is most desirable for clinical use of the compound.

FIGURE LEGENDS

FIG. 1. Synergistic activation of the 5-HT1A receptor promoter by NF-κB and human ERα. (A) COS-1 cells were transiently transfected with the −901luc reporter construct together with empty expression vector or expression vectors encoding the p50 and p65 subunits of NF-κB (white bars) in combination with expression vectors encoding ERα or ERβ (hatched bars) and treated with $10^{-8}$ M $E_2$ for 24 h (black bars). Depicted is the induction of luciferase activity evoked by NF-κB over cells transfected with empty expression vector. Bars represent the mean of at least three independent experiments ±S.D. (B) COS-1 cells were transiently transfected with 4xNF-κB(HIV)tkluc in combination with empty expression vector or expression vectors encoding the p50 and p65 subunits of NF-κB and expression vectors encoding ERα or ERβ. Cells were either untreated (white bars) or treated with $10^{-8}$ M $E_2$ (black bars) for 24 h. Depicted is the induction of luciferase activity evoked by NF-κB over cells transfected with empty expression vector. Bars represent the mean of at least three independent experiments ±S.D.

FIG. 2. Importance of κB elements in 5-HT1A receptor promoter regulation by NF-κB and human ERα. (A) Schematic representation of luciferase (luc) reporter constructs used, containing rat 5-HT1A receptor (5-HT1 AR) promoter deletions. The two open circles (O) represent NF-κB binding sites. (B) COS-1 cells were transiently transfected with the different reporter constructs as indicated, together with empty expression vector or expression vectors encoding the p50 and p65 subunits of NF-κB (white bars) in combination with expression vectors encoding ERα (hatched bars) and treated with $10^{-8}$ M $E_2$ for 24 h (black bars). Depicted is the induction of luciferase activity evoked by NF-κB over cells transfected with empty expression vector. Bars represent the mean of at least three independent experiments ±S.D.

FIG. 3. OH-T, but not ICI can enhance activity of the 5-HT1A receptor promoter by NF-κB and human ERα. (A) COS-1 cells were transiently transfected with the −901luc reporter construct together with empty expression vector or expression vectors encoding the p50 and p65 subunits of NF-κB in combination with expression vectors encoding ERα and treated with $E_2$. OH-T or ICI for 24 h as indicated. Depicted is the induction of luciferase activity evoked by NF-κB over cells transfected with empty expression vector. Bars represent the mean of at least three independent experiments ±S.D.

FIG. 4. The transactivation function of p65 is required for synergistic activation of the 5-HT1A receptor promoter by NF-κB and human ERα. COS-1 cells were transiently transfected with the −901luc reporter construct together with empty expression vector or expression vectors encoding p50, p65, p65RHD or p65Nsi as indicated (white bars) in combination with expression vectors encoding ERα (hatched bars) and treated with $10^{-8}$ M $E_2$ for 24 h (black bars). Depicted is the induction of luciferase activity evoked by the NF-κB subunits over cells transfected with empty expression vector. Bars represent the mean of at least three independent experiments ±S.D.

FIG. 5. The synergistic activation of the 5-HT1A receptor promoter by mouse ERα occurs in an AF-2 independent fashion. (A) COS-1 cells were transiently transfected with the −901luc reporter construct together with empty expression vector or expression vectors encoding the p50 and p65 subunits of NF-κB in combination with expression vectors encoding mouse ERα, ERβ, ERα 121–599, ERα 1–339 or ERα C241/244A. Cells were either untreated (hatched bars) or treated with $10^{-8}$ M $E_2$ (black bars) for 24 h. Depicted is the induction of luciferase activity evoked by NF-κB over cells transfected with empty expression vector. Bars represent the mean of at least three independent experiments ±S.D. (B) COS-1 cells were transiently transfected with 3xERE-JATAluc in combination with empty expression vector or expression vectors encoding mouse ERα, ERβ, ERα 121–599, ERα 1–339 or ERα C241/244A. Cells were either untreated (hatched bars) or treated with $10^{-8}$ M $E_2$ (black bars) for 24 h Depicted is the induction of luciferase activity evoked by ER over cells transfected with empty expression vector. Bars represent the mean of at least three independent experiments ±S.D.

FIG. 6. The A/B domain of ERα is essential for the synergistic activation of the 5HT1A receptor promoter. (A) COS-1 cells were transiently transfected with the −901luc reporter construct together with empty expression vector or expression vectors encoding the p50 and p65 subunits of NF-κB in combination with expression vectors encoding human ERα, ERβ, ERα/β or ERβ/α. Cells were either untreated (hatched bars) or treated with $10^{-8}$ M $E_2$ (black bars) for 24 h. Depicted is the induction of luciferase activity evoked by NF-κB over cells transfected with empty expression vector. Bars represent the mean of at least three independent experiments ±S.D. (B) COS-1 cells were transiently transfected with 3xERE-TATAluc in combination with empty expression vector or expression vectors encoding human ERα, ERβ, ERα/β or ERβ/α. Cells were either untreated (hatched bars) or treated with $10^{-8}$ M $E_2$ (black bars) for 24 h. Depicted is the induction of luciferase activity evoked by ER over cells transfected with empty expression vector. Bars represent the mean of at least three independent experiments ±S.D.

FIG. 7: Synergistic activation or transrepression of the E-selectin promoter by NF-κB's and respectively MR or ERα. (A) U-2 OS cells were transiently co-transfected with an E-selectin promoter-reporter and effects were measured of IL-1β, cotransfection of MR or a combination of IL-1β with MR in the absence or presence of 0.1 μM aldosteron. (B) U-2 OS cells were transiently co-transfected with a luciferase-reporter that does not contain the ELAM promoter and effects were measured of IL-1β, co-expression of MR, or a combination of IL-1β with MR in the absence or presence of 0.1 μM aldosteron. (C) U-2 OS cells were transiently co-transfected with an E-selectin promoter-reporter and effects were measured of IL-1β, co-transfection of ERα or a combination of IL-1β with ERα in the absence or presence of 0.1 μM 17β-estradiol. (D) U-2 OS cells were transiently transfected with a synthetic 3*NF-κB-tk promoter reporter and effects were measured of IL-1β, co-transfection of MR or a combination of IL-1β with MR in the absence or presence of 0.1 μM aldosteron. Results are expressed as fold induction in comparison to untreated cells (first bar in each figure). All values represent duplicates ±S.D. Note the difference in scales in A, B, C versus D.

EXAMPLES

Example 1

Materials and Methods Used

Special Reagents. 17β-estradiol was obtained from Sigma Chemical Co (St Louis, Mo.). 4-hydroxytamoxifen and ICI 164384 were kind gifts from Dr. A. Wakeling, Zeneca Pharmaceuticals, UK.

Cell Culture. Monkey COS-1 cells and human 293 embryonal kidney cells were obtained from American Type Culture Collection (ATCC; Rockville, Md.) and were cultured in a 1:1 mixture of DMEM and Ham's F-12 medium (DF; Life Technologies Inc.), buffered with bicarbonate and supplemented with 7.5% FCS. Dextran-coated charcoal (DCC)-FCS was prepared by treatment of FCS with dextran-coated charcoal to remove steroids, as described previously (25).

Plasmids. −901luc was created by partial digestion of −1588luc, a kind gift from Dr. O. Meijer (Leiden, the Netherlands), with StyI, filling-in and ligation into pGL3 digested with SmaI, redigestion with HindIII and religation; −81luc was created by digestion of −1588luc with StyI, filling-in and digestion with BgIII and ligation into pGL3 digested with SmaI/BgII; −901 365Mluc and −901 64Mluc were constructed by introducing point mutations into the original promoter constructs by site-directed mutagenesis using the oligonucleotides 5'-gagccgaattctacagactaa-3' (SEQ ID NO:1) and 5'-aactgcaaggagatctacatcgcccctcg-3' (SEQ ID NO:2), respectively. −901 365164Mluc was created by digestion of −901 64Mluc with SacII/HindIII and ligation into −901 365Mluc digested with SacII/HindIII; −81 64Mluc was made by partial digestion of −901 64Mluc with StyI and religation. The CMV4 expression vectors containing full length cDNAs encoding human p65 (RelA), p50 (NF-κB) and p65RHD (1–305), p65Nsi (1–551E391) have been described before (26, 27). The expression vectors encoding human ERα (pSG5-HEGO) and human ERβ (pSG5-ERβ530) were kind gifts of Dr. Chambon (Strasbourg, France) and Dr. Gustafsson (Stockholm, Sweden), respectively. Chimeric human ERα/ERβ and ERβ/ERα receptors were described (28) and contained the A/B domain of ERα and domain C, D, E, F of ERβ in the ERα/ERβ chimera, and contained the A/B domain of ERβ and domain C, D, E, F of ERα in the ERβ/ERα chimera. Mouse ERα (pMT2MOR), ERα 1–339, ERα 121–599 and ERα C241/244A (29) were kindly provided by Dr. Parker (Londen, UK). The reporter plasmids used 4xNF-κB(HIV)tkluc and 3xERE-TATA-luc have been described before (30, 31)

Transient Transfections. For transient transfections, COS-1 cells and 293 cells were cultured in 24-well plates in DF+ supplemented with 5% DCC-FCS. Cells were transfected using calcium-phosphate coprecipitation with 0.4 ug of luciferase reporter, 0.6 ug of PDMIacZ and 0.2 ug of the indicated expression plasmids. pBluescript SK⁻ was added to obtain a total amount of 1.8 ug of DNA/well. After 16 h, the medium was refreshed and when indicated hormone was added. Cells were harvested 24 h later and assayed for luciferase activity using the Luclite luciferase reporter gene assay kit (Packard Instruments, Conn.) according to the manufacturer's protocol and the Topcount liquid scintillation counter (Packard Instruments, Conn.). Values were corrected for transfection efficiency by measuring beta-galactosidase activity (32).

Example 2

Synergistic Activation of the 5-HT1 A Receptor Promoter by NF-κB and ER.

Figure 1:
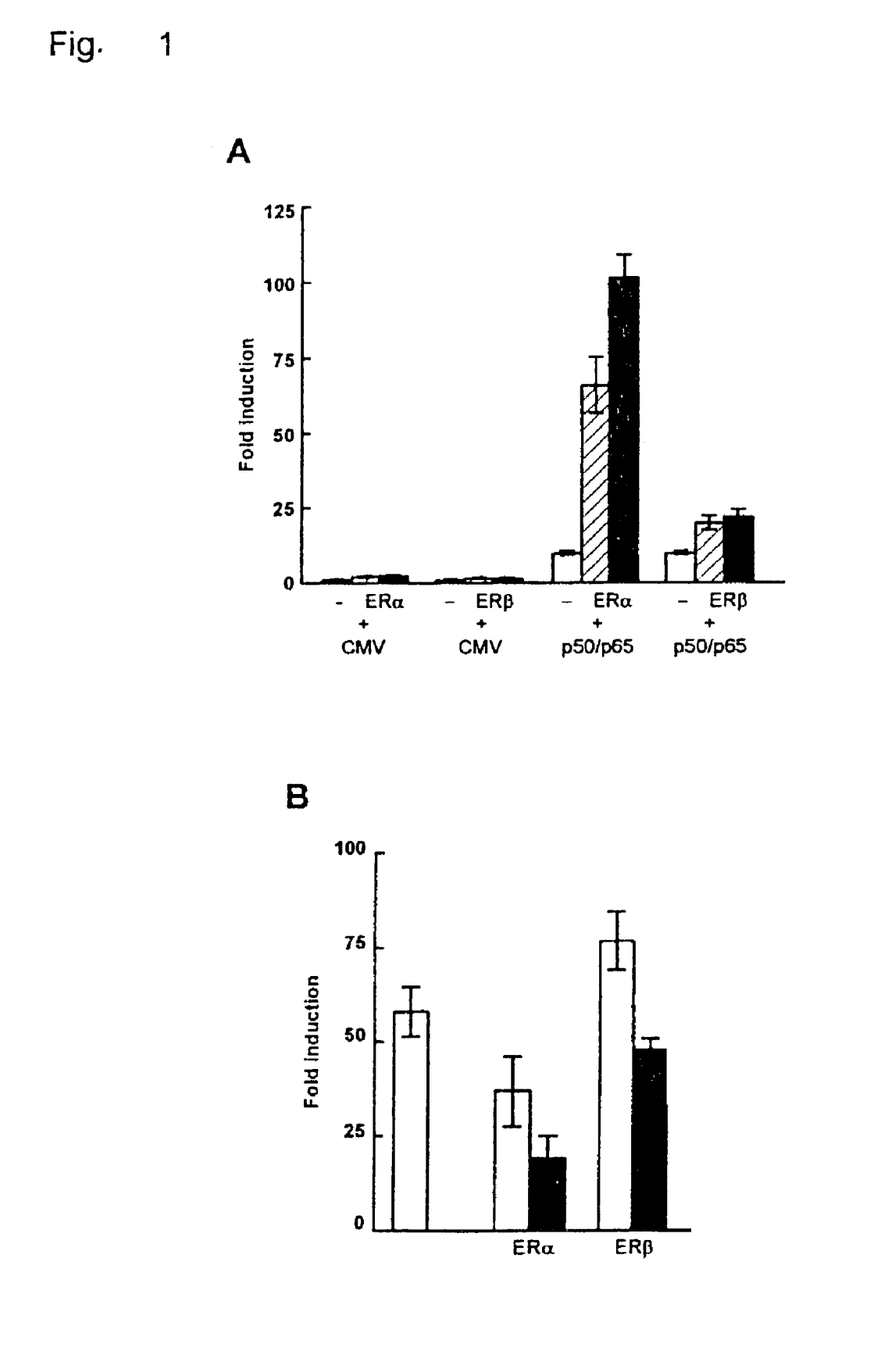

To determine the effect of estrogens on 5-HT1A receptor promoter activity, we transiently transfected COS-1 cells with a reporter construct containing the 5-HT1A receptor promoter together with an expression vector encoding ERα or ERβ. As shown in FIG. 1A, cotransfection of ERα or ERβ and treatment of the cells with 17β-estradiol ($E_2$) hardly had an effect on 5-HT1A promoter activity. However, besides direct regulation, ER target genes can also be regulated indirectly through interaction of ER with other transcription factors. Putative NF-κB binding sites were shown to be present in the −901luc 5-HT1A receptor promoter construct (see FIG. 2A) and transfection of this reporter construct with expression vectors encoding the p50 and p65 subunit of NF-κB resulted in an 10-fold induction of the reporter. Interestingly, cotransfection of ERα in combination with NF-κB now resulted in an enormous induction of promoter activity, which could be further increased by the addition of $E_2$ (FIG. 1A). In contrast to ERα, ERβ showed a much smaller induction when cotransfected with NF-κB and no effect of $E_2$ could be observed. Similar results were obtained in 293 cells (results not shown), although the level of activation by ERα was less high compared to COS-1 cells. These results indicate that the 5-HT1A receptor promoter can be synergistically activated by NF-κB and ER.

In the past several groups have reported an inhibitory effect of estrogens on NF-κB activity (33–35). Therefore, we also studied the effect of estrogen on a reporter construct containing four NF-κB elements from the HIV-LTR in front of the thymidine kinase promoter coupled to luciferase in combination with expression constructs encoding ERα or ERβ and the p50 and p65 subunits of NF-κB. On this reporter construct, cotransfection of ERα resulted in repression of the transcriptional activity of NF-κB already in the absence of hormone, while addition of hormone resulted in a further repression (FIG. 1B). Cotransfection of ERβ also showed some repression of NF-κB activity. Similar results were obtained in 293 cells (results not shown). These results indicate that while ER acts as a transcriptional repressor of NF-κB on an synthetic NF-κB reporter construct that is based on a consensus response element from the ICAM promoter, ER acts as a transcriptional activator with NF-κB on the 5HT1A receptor promoter.

Example 3

Involvement of NF-κB Elements in 5-HT1A Receptor Promoter Regulation by NF-κB and ER.

Figure 2:
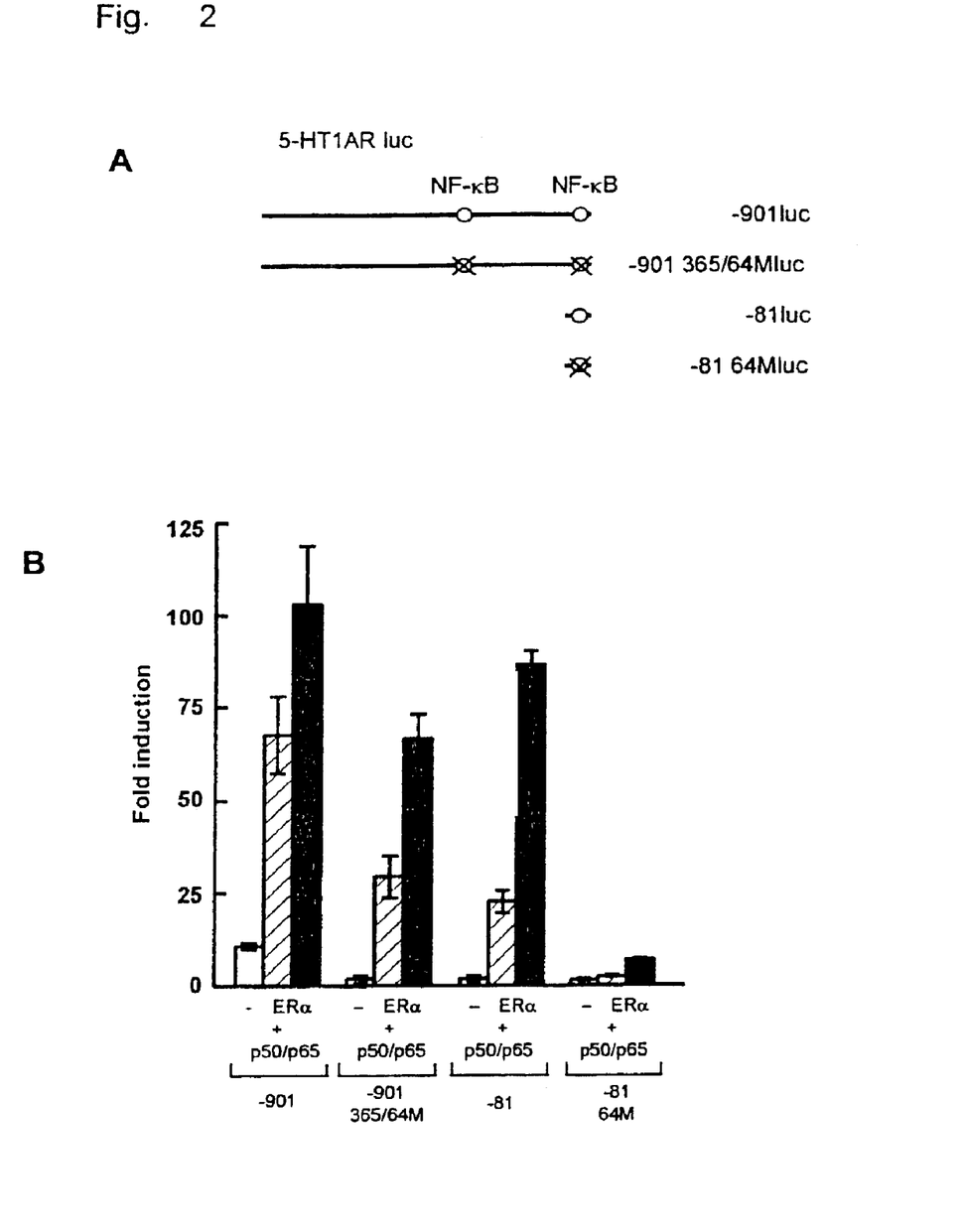

To localize the effect of ER on the 5-HT1A receptor promoter, several promoter deletion constructs were used (FIG. 2A). Mutation of both NF-κB elements (−901 365/64Mluc) completely abolished the effect of NF-κB on the 5-HT1A receptor promoter (FIG. 2B). However, ERα, only in combination with NF-κB, was still able to induce promoter activity as efficient as on the wild type promoter (−901 luc). Likewise, the promoter construct 481luc could not be induced by NF-κB, although it still contained one NF-κB element. However, also on this promoter construct, the effect of ERα with NF-κB was maintained. When the single NF-κB element present in the −81luc construct was mutated (−81 64Mluc), the ERα effect was almost completely abolished. Thus, synergistic activation of the 5-HT1A receptor promoter involves NF-κB binding sites, although activation of the promoter by NF-κB itself appears not to be required for the effect of ER. These results suggest that this synergistic promoter activation by ER is independent of DNA-binding and involves protein-protein interactions.

Example 4

Effects of Anti-Estrogens on the 5-HT1A Receptor Promoter.

Figure 3:
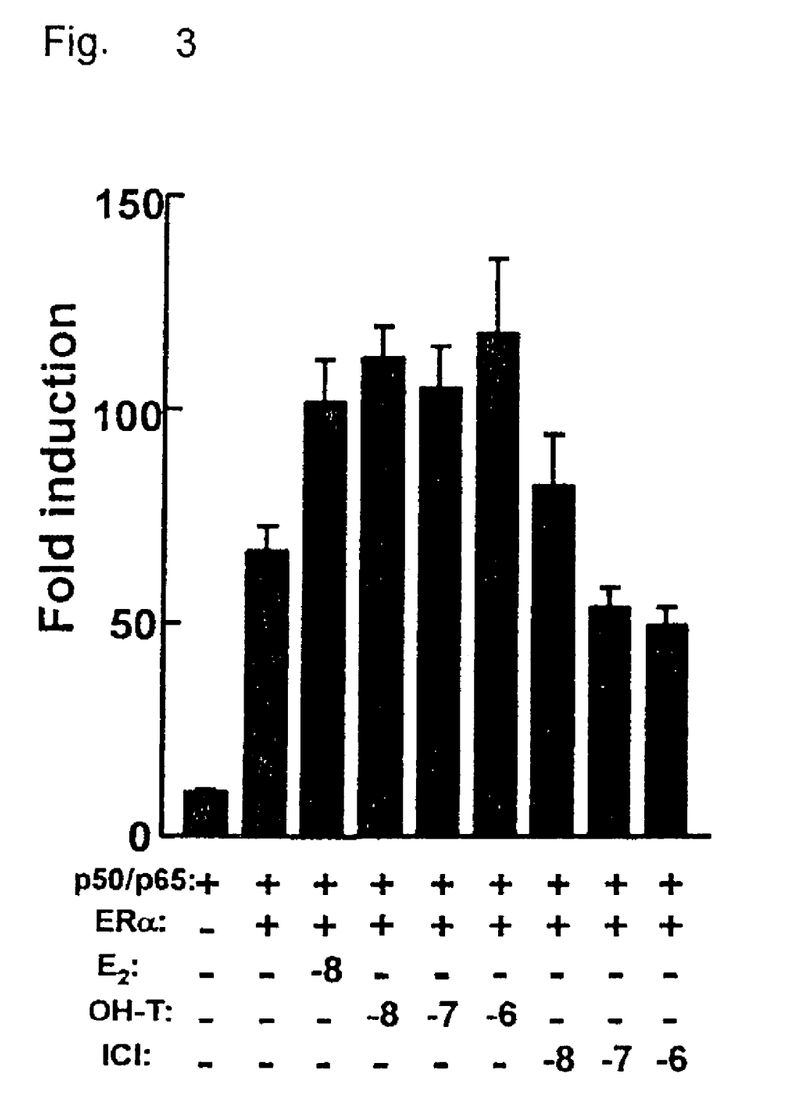

Anti-estrogens have been described to have differential effects depending on promoter context and receptor subtype. In transactivation experiments, OH-T inhibited transcription of genes regulated by a classical ERE, while it activated, like $E_2$, transcription of genes that are under the control of an AP-1 element with ERα (22). We examined the effect of anti-estrogens on the 5-HT1A receptor promoter using the partial antagonist OH-T, which blocks AF-2, and the "pure" antagonist ICI 164384 (ICI), which blocks AF-1 and AF-2. As shown in FIG. 3, ICI treatment did not enhance the activity of the 5-HT1A receptor promoter by ERα and NF-κB, while OH-T was as potent as $E_2$ in transcriptional activation. These data indicate that the partial antagonist OH-T, still able to activate AF-1, is as potent as $E_2$ in synergistic activation of the 5-HT1A receptor promoter by ERα.

Example 5

Domains of NF-κB and ER Involved in the Synergistic Activation of the 5-HT1A Receptor Promoter.

Figure 4:
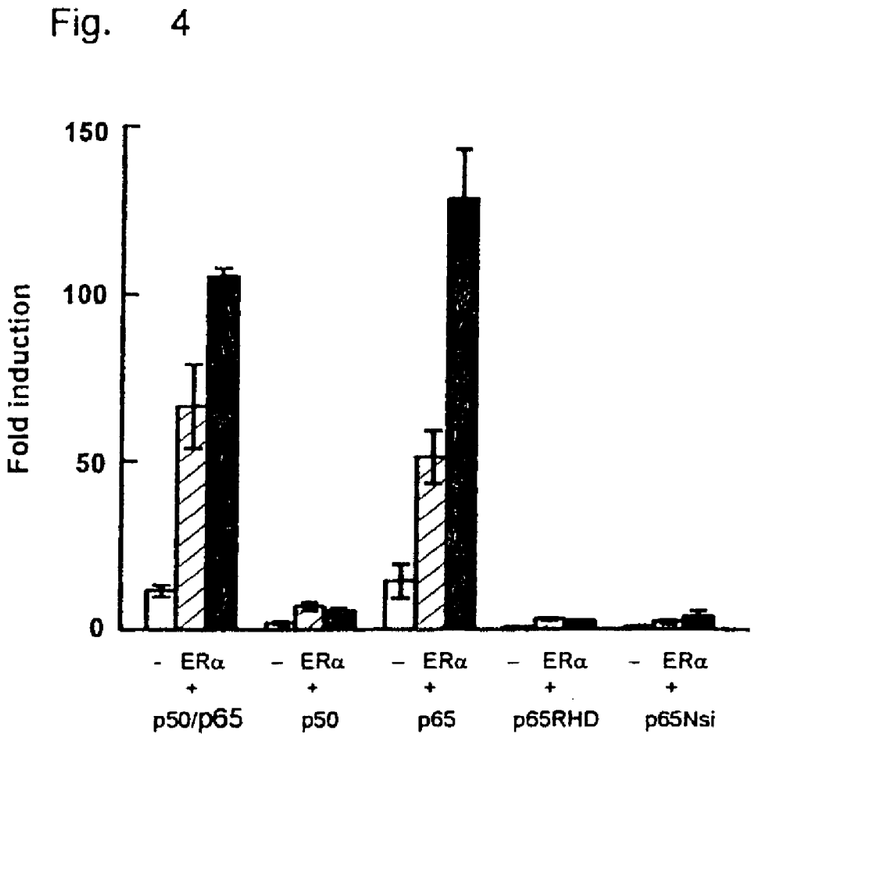

To determine the importance of the transactivation function of NF-κB, we examined the effect of deleting the transactivation domains or impairing the DNA-binding function of the p65 subunit of NF-κB, on its ability to synergistically activate the 5HT1A receptor promoter with ER in a transient transfection assay. While cotransfection of p50 and p65 or p65 alone strongly activated the promoter in combination with ERα and $E_2$, cotransfection of p50 alone, which has no transactivation function, hardly had an effect. Deletion of the transactivation domains of p65 resulted in a construct containing only the Rel homology domain (p65RHD). P65RHD was still able to bind to DNA (27), but was unable to activate the promoter both in the absence or presence of ERα and E$_2$. The DNA-binding defective mutant p65Nsi) still contained intact transactivation domains, but was also unable to synergistically activate the promoter. Taken together, these data show that both the transactivation function as well as the DNA binding function of p65 are essential for synergistic activation of the 5-HT1 A receptor promoter by ER.

Figure 5:
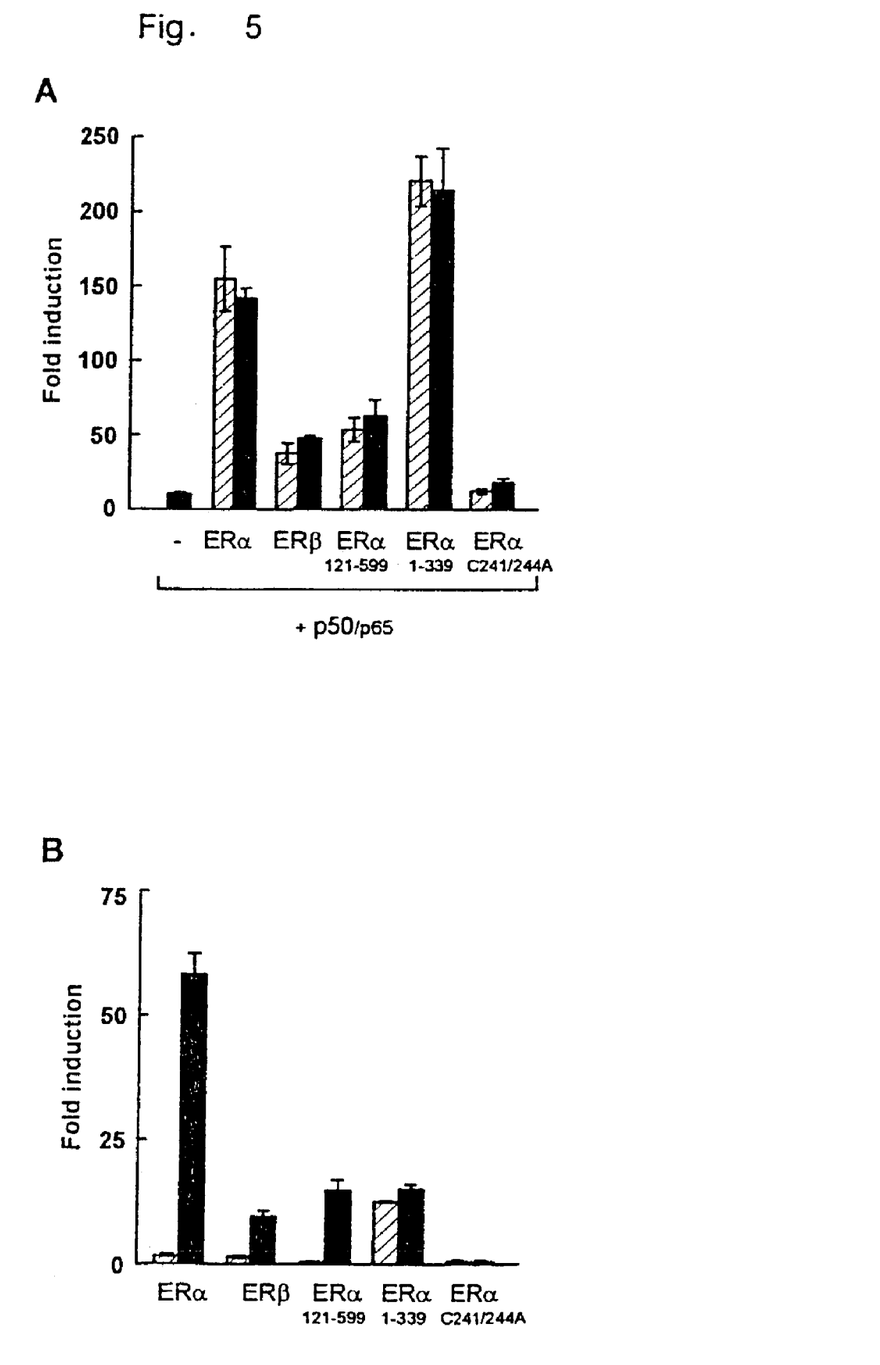

To identify the regions of ERα involved in activation of the 5-HT1A receptor promoter, deletion constructs of mouse ERα were used, which lack part of the A/B region, containing AF-1, or which lack part of the ligand binding region, containing AF-2. While deletion of the A/B region (ERα 121–599) completely abolished the synergistic activation of the promoter, deletion of the ligand binding domain (ERα 1339) resulted in a receptor which was at least as active as wildtype ERα (FIG. 5A). The DNA-binding defective mutant of ERα (ERα C241/244A) was unable to activate the 5-HT1A receptor promoter, possibly because a functional DNA binding domain is needed for interaction with NF-κB (34). Note that in contrast to human ERα, no ligand dependency can be observed for mouse ERα in synergistic activation of the 5HT1A receptor promoter. This synergistic activation of the promoter by ERα could only be observed in combination with NF-κB, although in the absence of NF-κB a small activation of the promoter could be found with ERα 1–339 (results not shown). In a control experiment, ERα, ERβ and the deletion mutants were cotransfected with a reporter construct containing three copies of a consensus ERE and a TATA box coupled to luciferase to determine their ability to activate transcription from a classical ERE. As shown in FIG. 5B, both ERα and ERβ stimulate transcription from 3xERE-TATA-luc, although the transcriptional activity of ERβ was significantly less than that of ERα, a phenomenon which has been described before (28). Both deletion mutants, lacking either AF-1 or AF-2, stimulated transcription although much less efficiently than wildtype ERα, indicating that the transactivation domains are able to synergize on this promoter construct. Furthermore, it was shown that ERα 1339 was already maximally activated in the absence of ligand, clearly demonstrating the ligand-independent activity of AF-1. As expected, the DNA-binding defective mutant, ERα C241/244A, was unable to activate this reporter construct.

Figure 6:
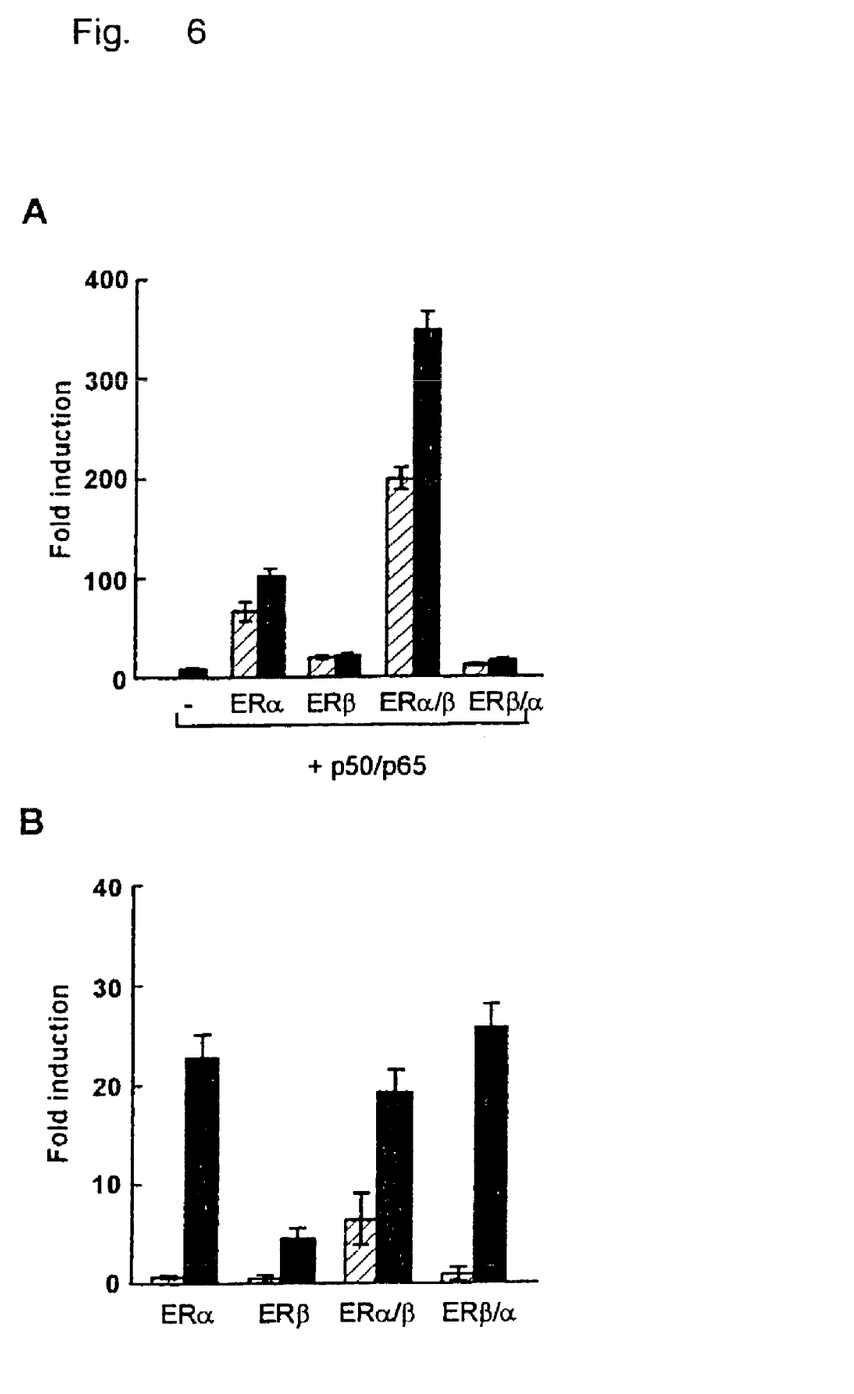

Since differences between ERα and ERβ were observed with respect to their potency in activation of the 5-HT1A receptor promoter, chimeric constructs with ERα sand ERβ were used to further determine the regions of ERα and ERβ involved in this activation. Replacement of the A/B region of ERβ with the A/B region of ERα (ERα/β) resulted in a chimeric receptor which was even more potent than wildtype ERα in activation of the 5-HT1A receptor promoter (FIG. 6A). However, replacement of the A/B region of ERα with the A/B region of ERβ (ERβ/α) almost completely abolished the ability of the receptor to synergistically activate the promoter. Again this synergistic activation of the promoter by ERα and ERα/β could only be observed in combination with NF-κB, although in the absence of NF-κB a small ligand-independent activation of the promoter could be seen with ERα/β (results not shown). In a control experiment, both chimeric constructs were able to activate transcription from 3xERE-TATA-luc as efficiently as wildtype ERα, while some ligand-independent activity could be only observed with ERα/β (FIG. 6B). These results suggest that the synergistic activation of the 5-HT1A receptor promoter by ER α and NF-κB is dependent on the DNA binding domain and the A/B region of ERα, containing AF-1. In summary, estrogen exerts profound effects on mood and mental state. The ability of estrogen to modulate serotonergic function raises the possibility that it may play a role in the mechanism associated with depression and its treatment. A cellular mechanism for estrogen to influence mood might be through the regulation of genes involved at various levels of the serotonin system. Here we report that estrogen can upregulate the expression of the serotonin-1A receptor via a new mechanism involving synergistic activation by NF-κB with estrogen receptor. The partial antiestrogen 4-hydroxytamoxifen had the same effect as estrogen. In addition, mutation analysis showed that both the transactivation function of p65 and activation function 1 of estrogen receptor a were essential for this synergistic regulation. Therefore, we propose that NF-κB complexes cooperate with estrogen receptor to recruit cofactors into the complex and thereby synergistically activate the serotonin-1A receptor promoter through nonclassical estrogen response elements by a mechanism that does not involve direct receptor binding to DNA.

Example 6

Materials and Methods

Special Reagents. Aldosteron (N. V. Organon) was used at a concentration of 0.1 μM. Recombinant human IL-1β was purchased at Genzyme and was used in a concentration of 100 u/ml.

Cell Culture. Human osteosarcoma U-2 OS cells were obtained from American Type Culture Collection (ATCC; Rockville, Md.) and were cultured in M505, a 1:1 mixture of phenolred-free DMEM and Ham's F-12 medium (DF; Life Technologies Inc.), buffered with bicarbonate and supplemented with 10% FCS.

Plasmids.

pGL3-ELAM was constructed by cloning part of the E-Selectin promoter into the Sac I and Xho I sites of pGL3-basict (Promega). The E-selectin promoter region was obtained by PCR on human genomic DNA using the oligonucleotide primers 5'-ctgcagatctgagtttctgacatcaftgta-3' (SEQ ID NO:5) and 5'-atcaftcgaagaagtcagccaagaacagct-3' (SEQ ID NO:6). The PCR product was subcloned in pCR™2.1 (TA-Cloning kit, Invitrogen), digested with Sac I and Xho I and subsequently ligated into pGL3-basic.

The luciferase reporter plasmid 3*NF-κB-TK was constructed by inserting three repeats of the NF-κB binding site from the ICAM promoter (van de Stolpe, A., Caldenhoven, E., Stade, B. G., Koendermans, L., Raaijmakers, J. A. M., Johnson, J. P. & van der Saag, P. T. (1994) J. Biol. Chem. 269: 6185–6192.) in front of the herpes simplex virus thymidine kinase (HSV-TK) promoter. The TK promoter was cloned into the Bgl II-site of pGL3-basic (Promega). The triple repeat of NF-κB binding sites was constructed by annealing the oligonucleotide primers 5'-catacggtaagct-tggggtcatcgccctgccaccgccgcccgattgctttagcttggaaattccgga-3' (SEQ ID NO:3) and 5'-gtatgccaaagcttctccggaatttc-caagctccggaatttccaagctccggaatttccaagctaaa-3' (SEQ ID NO:4) followed by PRC amplification and subcloning in the pCR™2.1 vector. The insert was excised using HindIII, blunted with Klenow DNA polymerase and ligated into the SmaI site of pGL3-tk-luc.

The pNGV1-hMR expression vector contains the wild type human MR under control of the SV40 promoter and the PKCRE-ERα expression vector contains the wild type human ER under control of the SV40 promoter.

Transient Transfections.

For transient transfections, U-2 OS cells were seeded in 6-well plates. After two or three days the cells were transfected with reporter, expression vectors and β-galactosidase control vector. Two different experimental settings were used. For testing the synergistic effects of MR with IL-1β, cells were transfected with 1 μg pGL3-ELAM or 3*NF-κB-TK, 1 μg pNGV1-hMR or 1 μg of PKCRE-ERα and 0.25 μg of β-galactosidase control plasmid. Different amounts of transfected DNA were corrected with expression vector without insert. Transient transfection was performed using lipofectin reagent (Life Technologies). Transient transfections with lipofectin were performed according to the suggestions of the manufacturer, with some minor changes. Per μg of DNA to be transfected, 5 μl of lipofectin was used and cells were incubated with the transfection mixture during 5 hours, after which the transfection mix was aspirated and replaced by M505+10% DCC-FCS. The transfected cells were incubated overnight with test compounds (e.g. different combinations of IL-1β, dexamethason and aldosteron) prior to cell lysis. Measurement of luciferase and β-galactosidase activity were performed using respectively the luciferase assay system (Promega) and Galacto-light plus (Tropix) according to the manufacturers' protocols and measured on the Victor 1420 multilabel counter, Wallac. Detection of β-galactosidase activity was used as a control for transfection efficiency.

REFERENCES

McEwen; B. S., & Alves, S. E. (1999) *Endocr. Rev.* 20, 279–307

Bethea, C. L., Pecins-Thompson, M., Schutzer W. E., Gundlah, C., & Lu, Z. N. (1998) *Mol. Neurobiol.* 18, 87–123.

Joffe, H., & Cohen L. S. (1998) *Biol. Psychiatry* 44, 798–811.

Buhot, M. C. (1997) *Curr. opin. Neurobiol.* 7, 243–254.

Murphy, D. L. (1990) *Neuropsychopharmacology* 3, 457–471.

Maes, M. & Meltzer, H. (1995) in *The Serotonin Hypothesis of Depression.*, eds. Bloom, F. & Kupfer, D. (Raven, New York) pp. 933–944.

Julius, D. (1991) *Annu. Rev. Neurosci.* 14, 335–360.

Fargin, A., Raymond, J. R., Regan, J. W. Cotecchia, S., Lefkowitz, R. J. & Caron, M. G. (1989) *J. Biol. Chem.* 264, 14848–14852.

Albert, P. R., Zhou, Q-Y., Van Tol, H. H. M., Bunzow, J. R., & Civelli, O. (1990) *J. Biol. Chem.* 265, 5825–5832.

Chalmers, D. T. & Watson, S. J. (1991) *Brain Res.* 561, 51–60.

Pompeiano, M., Palaios, J. M., & Mengod, G. (1992) *J. Neurosci.* 12, 440453.

Biegon, A., & McEwen, B. S. (1982) *J. Neurosci.* 2, 199–205.

Fink, G., Sumner, B. E., McQueen, J. K., Wilson, H., & Rosie, R. (1998) *Clin. Exp. Pharmacol. Physiol.* 25, 764–775.

McQueen, J. K., Wilson, H., & Fink, G. (1997) *Brain Res. Mol. Brain Res.* 45, 13–23.

Green, S., Walter, p., Kumar, V., Krust, A., Bornet, J. M., Argos, P., & Chambon, P. (1986) *Nature* 320, 134–139.

Greene, G. L., Gilna, P., Waterfield, M., Baker, A., Hort, Y., & Shine, J. (1986) *Science* 231, 1150–1154.

Kuiper, G. G. J. M., Enmark, E. Pelto-Huikko, M., Nilsson, S., & Gustafsson, J.-Å., (1996) *Proc. Natl. Acad. Sci. USA* 93, 5925–5930.

Mosselman, S., Polman, J., & Dijkema, R. (1996) *FEBS lett.* 392, 49–53.

Tora, I., White, J., Brou, C., Tasset, D., Webster, N., Scheer, E., & Chambon, P. (1989) *Cell* 59, 477–487.

Tzukerrnan, M. T., Esty, A., Santiso-Mere, D., Danielian, P., Parker, M. G., Stein, R. B., Pike, J. W., & McDonnell, D. P. (1994) *Mol. Endocinol.* 8, 21–30.

Elgort, M. G., Zou, A., Marschke, K. B., & Allegretto, E. A. (1996) *Mol. Endocrinol* 10, 477–487.

Webb, P., Lopez, G. N., Uht, R. M., & Kushner, P. J. (1995) *Mol. Endocrinol.* 9, 443–456.

Krishnan, V., Wang, X., & Safe, S. (1994) *J. Biol. Chem.* 269, 15912–15917.

Stein, B., & Yang, M. X. (1995) *Mol. Cell. Biol.* 15, 4971–4979.

Van der Burg, B., Rutteman, G. R., Blankenstijn, M. A., De Laat, S. W., & van Zoelen E. J. J. (1988) *J. Cell. Physiol.* 123, 101–108.

Caldenhoven, E., Liden, J., Wissink, S., Van de Stolpe, A., Raaijmakers, J., Okret, S., Gustafsson, J.-Å., & Van der Saag, P. T. (1995) *Mol Endocrinol.* 9, 401–412.

Wissink, S., Van Heerde, E. C., Schmitz, M. L., Kalkhoven, E., Van der Burg, B., Baeuerle, P. A., & Van der Saag, P. T. (1997) *J. Biol. Chem.* 272, 22278–22284.

McInerney, E. M., Weis, K. E., Sun, J., Mosselman, S., & Katzenellenbogen, B. S. (1998) *Endocrinology* 139, 4513–4522.

Danielian, P. S., White, R., Lees, J. A., & Parker, M. G. (1992) *EMBO J.* 11, 1025–1033.

Wissink, S., Van de Stolpe, A., Caldenhoven, E., Koenderman, L., & Van der Saag, P. T. (1997) *Immunobiol.* 198, 50–64.

Legler, J., Van den Brink, C. E., Brouwer, A., Murk, A. J., Van der Saag, P. T., Vethaak, A. D., & Van der Burg, B. (1999) *Toxicol. Sci.* 48, 55–66.

Pfahl, M., Tzukerman, M., Zhang, X.-K., Lehman, J. M., Hermann, T., Wills, K. N., & Graupner, G. (1990) *Methods Enzymol.* 189, 256–270.

Ray, A., Prefontaine, K. E., & Ray, P. (1994) *J. Biol. Chem.* 269, 12940–12946.

Stein, B., & Yang, M. X. (1995) *Mol. Cell. Biol.* 15, 4971–4979.

Galien, R., Evans, H. F., & Garcia, T. (1996) *Mol Endocrinol.* 10, 713–722.

Paech, K., Webb, P., Kuiper, G. G. J. M., Nilsson, S., Gustafsson, J.-Å, Kushner, P. J., & Scanlan, T. (1997) *Science* 277, 1508–1510.

Jonat, C., Rahmsdorf, H. J., Park, K. K., Cato, A. C. B., Gebel, S., Ponta, H., & Herrich, P. (1990) *Cell* 62, 1189–1204.

Harrison, R. J., McNeil, G. P., & Dobner, P. R. (1995) *Mol. Endocrinol.* 9, 981–993.

Weigel, N. L., & Zhang, Y. (1998) *J. Mol. Med.* 76, 469–479.

Le Goff, P., Montano, M. M., Schodin, D. J., & Katzenellenbogen, B. S. (1994) *J. Biol. Chem.* 11, 4458–4466.

Kato, S., Endoh, H., Masuhiro, Y., Kitamoto, T., Uchiyama, S., Sasaki, H., Masushige, S., Gotoh, Y., Nishida, E., Kawashima, H., Metzger, D., & Chambon, P. (1995) *Science* 270, 1491–1594.

Tremblay, A., Tremblay, G. B., Labrie, F., & Giguere, V. (1999) *Mol. Cell* 3, 513–519.

Hu, E., Kim, J. B., Sarraf, P., & Spiegelman, B. M. (1996) *Science* 274, 2100–2103.

Gitlin, M. J., & Pasnau, R. O. (1989) *Am. J. Psychiatry* 146, 1413–1422.

Oppenheim G. (1983) *Biol. Psychiatry* 18, 721–725.

Gregoire, A. J., Kumar, R., Everitt, B., Henderson, A. F., & Studd, J. W. (1996) *Lancet* 347, 930–933.

Shughrue, P. J., Lane, M. V., & Merchenthaler, I. (1997) *J. Comp. Neurol.* 4, 507–525.

Schmidt-Ullrich, R., Memet, S., Lilienbaum, A., Feuillard, J., Raphael, M., & Israel, A. (1996) *Development* 122, 2117–2128.

X O'Neill, L. A. J., & Kaltschmidt, C. (1997) *Trends Neurosci.* 20, 252–258.

We claim:

1. A method for the identification of compounds capable of modulating a synergistic effect of a steroid receptor and a Rel protein on regulatory elements, comprising the steps of:

providing a cell comprising a regulatory element capable of being synergistically activated by a steroid receptor and a Rel protein, said cell additionally comprising sufficient levels of said steroid receptor and said Rel protein to allow synergistic activation of the regulatory element;

contacting said cell with at least one compound; and, determining whether the activation of the regulatory element is modulated by the compound.

2. The method according to claim 1, wherein said steroid receptor is selected from the group consisting of the estrogen receptor α, the estrogen receptor β, and the mineralocorticoid receptor.

3. The method according to claim 1, wherein the Rel protein is selected from the group consisting of NF-κB1, Lyt-10, cRel, RelA and RelB.

4. The method according to claim 1, wherein the regulatory element is a promoter for the 5-HT1A receptor gene.

5. The method according to claim 1, wherein said cell is transfected with a reporter gene capable of signaling the activation of the regulatory element.

6. A cell transfected with a nucleic acid comprising a promoter for the 5-HT1A receptor gene and a reporter gene capable of signaling the activation of the promoter for the 5-HT1A reporter gene, said cell further comprising:

a nucleic acid encoding a steroid receptor and capable of functionally expressing said steroid receptor within said cell, and a nucleic acid encoding a Rel protein and capable of functionally expressing said Rel protein within said cell.

7. The cell according to claim 6, wherein said steroid receptor is selected from the group consisting of the estrogen receptor α, the estrogen receptor β, and the mineralocorticoid receptor.

8. The cell according to claim 6, wherein the Rel protein is selected from the group consisting of NF-κB1, Lyt-10, cRel, RelA and RelB.

9. The cell according to claim 6, wherein at least one of the nucleic acid comprising a promoter for the 5-HT1A receptor gene, the nucleic acid encoding a steroid receptor, and the nucleic acid encoding a Rel protein is transfected into the cell.

10. The method according to claim 1, wherein at least one of the regulatory element, a nucleic acid encoding the steroid receptor, and a nucleic acid encoding the Rel protein are transfected into the cell.

* * * * *